United States Patent [19]

Moore

[11] 4,133,733

[45] Jan. 9, 1979

[54] ELECTROLYTIC TITRATION APPARATUS

[75] Inventor: Robert T. Moore, Palo Alto, Calif.

[73] Assignee: Envirotech Corporation, Menlo Park, Calif.

[21] Appl. No.: 807,479

[22] Filed: Jun. 17, 1977

[51] Int. Cl.² ........................................... G01N 27/44
[52] U.S. Cl. ............................................. 204/195 T
[58] Field of Search ..................... 204/195 T, 1 M; 73/23.1, 61.1 C

[56] References Cited

U.S. PATENT DOCUMENTS

| 2,624,701 | 1/1953 | Austin | 204/195 T |
|---|---|---|---|
| 2,745,804 | 5/1956 | Shaffer, Jr. | 204/195 T |
| 2,928,774 | 3/1960 | Leisey | 204/195 T X |
| 3,032,493 | 5/1962 | Coulson et al. | 204/195 T |
| 3,131,348 | 4/1964 | Taylor et al. | 204/195 T X |
| 3,338,812 | 8/1967 | Dworak et al. | 204/195 T |
| 3,427,238 | 2/1969 | Myers et al. | 204/195 T |
| 3,563,875 | 2/1971 | Coulson | 204/195 T |
| 3,580,832 | 5/1971 | Rhodes | 204/195 T |

*Primary Examiner*—G. L. Kaplan
*Attorney, Agent, or Firm*—Robert E. Krebs

[57] ABSTRACT

An electrolytic titration cell of an electrolytic titration apparatus includes a reaction chamber without baffles and means for introducing gas as the means to mix electrolyte contained in the chamber. The cell further includes means for maintaining a constant level of electrolyte in the reaction chamber and electrodes removably mounted by means of septa.

19 Claims, 8 Drawing Figures

ELECTROLYTIC TITRATION APPARATUS

BACKGROUND OF THE INVENTION

1. Field of the Art

The present invention relates to an electrolytic titration apparatus and, more particularly, to an electrolytic cell for use in the apparatus.

2. State of the Art

It is well known that constituents produced in gas chromatography can be continuously measured in an electrolytic titration apparatus such as disclosed in U.S. Pat. No. 3,427,238 to Myers et al. Typically, such measurements must be made in about thirty seconds and must be precise to about 0.1 nanograms.

There are certain drawbacks with the Myers et al cell when it is operated in a mode to achieve the above mentioned titration time and sensitivity requirements. With the Myers et al cell, it is necessary to precisely adjust the cap which positions the sensor and working electrodes and to hold constant the gas input rate and the magnetic stir rate. Unfortunately, the electrolyte is evaporated from the cell during operation and a means for continuously replenishing the electrolyte in the Myers et al cell without lengthening the titration time and lessening the sensitivity has not been known.

Preventing the Myers et al and other titration cells in general from having easily achieved low titration times and sensitivity is the volume of electrolyte necessary for operation of the cells in question. Rapid titration times and greater sensitivities have been achieved by Myers and others by placing their sensor electrodes in close and precise proximity with the location at which the sample is introduced to the titration cell and attempting to average electrical noise caused by localized concentration effects. The noise has been reduced to a degree by use of rectangular electrode surfaces which add to cell size and by critical adjustment of the sensor electrode position.

These prior electrolytic cells, including the Myers et al cell, have not been capable of operation with cell electrolyte volumes of less than about five milliliters. The minimum size of the Myers et al cell, which is typical of prior art cells, is dictated by the presence of glass-to-metal seals for the electrodes to prevent contamination, square electrode surfaces and a stirring means such as a electrolyte stirring means.

The construction of prior electrolytic titration cells has also been complicated by the placement of fritted glass, fiber wick and other diffusion limiting means between the reaction chamber and a compartment in which the reference electrode is mounted.

OBJECTS OF THE INVENTION

An object of this invention is to provide an electrolytic titration cell of simple construction and small size for an electrolytic titration apparatus, the cell having sufficient sensitivity and titration times, without depending on localized concentration effects to be suitable for analyzing constituents produced in gas chromatography analysis.

Another object is to provide an electrolytic titration cell with means for stirring the electrolyte with gas without baffles distributing the electrolyte in the chamber.

Yet another object is to provide an electrolytic titration cell with means for maintaining a constant level of electrolyte within the chamber such that the electrolyte volume in the chamber is less than about 3 milliliters.

Further objects include providing an electrolytic titration cell in which the electrodes and tubing entering the chamber can be removably mounted through septa; in which the sensor electrode, one of the generating electrodes and the location at which the carrier gas introduces the sample are oriented one above the other, at the center of the chamber; and in which the compartment, in which the reference electrode is mounted, is in electrolytic communication with the chamber through an open capillary.

BRIEF DESCRIPTION OF THE DRAWINGS

Further objects and advantages of the invention may be readily ascertained by reference to the following description and attached drawings, which are offered for description only and not in limitation of the invention, the scope of which is defined in the appended claims.

In the drawings.

PREFERRED EMBODIMENT OF THE INVENTION

Figure 2:
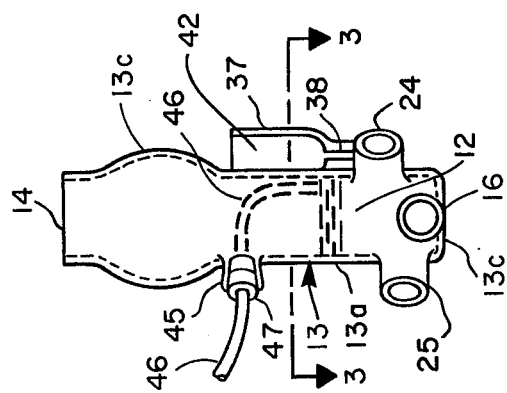
FIG. 2 is another side view of the vessel not including the drain tube of FIG. 1 in which the vessel has been rotated 90° about a vertical axis.
Figure 1:
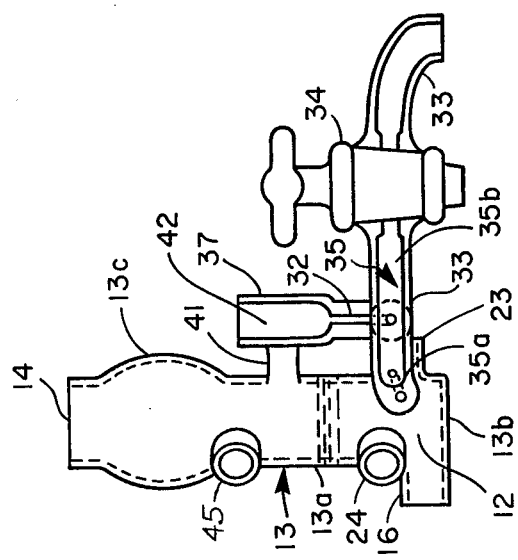
FIG. 1 is a side view of an electrolytic vessel of an electrolytic titration cell according to the present invention with a portion in cross section.

The electrolytic titration cell shown in the drawings forms a part of an electrolytic titration apparatus and includes means for containing an electrolyte and defines a chamber 12 for carrying out the titration reaction. Referring to FIGS. 1 and 2, this means is shown without the associated electrodes and tube connections and includes a substantially cylindrical vessel 13. Preferably, the vessel 13 is formed of clear glass to allow bubbles to be seen and the placement of electrodes in the cell to be observed. As can be seen, the vessel 13 has a straight-sided cylindrical portion 13a to define the chamber 12 for containing liquid electrolyte. The chamber 12 is formed without baffles for distributing electrolyte in the chamber 12. The cylindrical portion 13a is formed integral with a flat bottom 13b and a conventional bubble break chamber 13c above the cylindrical portion 13a. The top 14 of the vessel 13 is open and serves as a gas discharge port.

To introduce a carrier fluid containing a constituent to be titrated into the chamber 12 to the contained electrolyte, the vessel 13 has a gas inlet port 16 formed through the cylindrical portion 13a, preferably at the bottom of the chamber 12. An inlet tube 17 (FIG. 4) is removably mounted to extend through a septa 18 fixed in the gas inlet port 16. The inlet tube 17 extends into the chamber 12 to a location away from the sides of the chamber 12 and preferably at the bottom and center (axis) of the chamber 12. Carrier fluid containing a constituent to be titrated is introduced through the inlet tube 17. It is preferred that the carrier fluid be a gas unreactive with respect to the electrolyte and the gas be continuously introduced regardless of the need to introduce constituent so that the gas introduction serves as the primary means for stirring the contained electrolyte to provide sufficient mixing in the chamber 12. A separate gas inlet port to the vessel 13 with a tube and septa could be utilized to introduce a separate gas for stirring.

Figure 4:
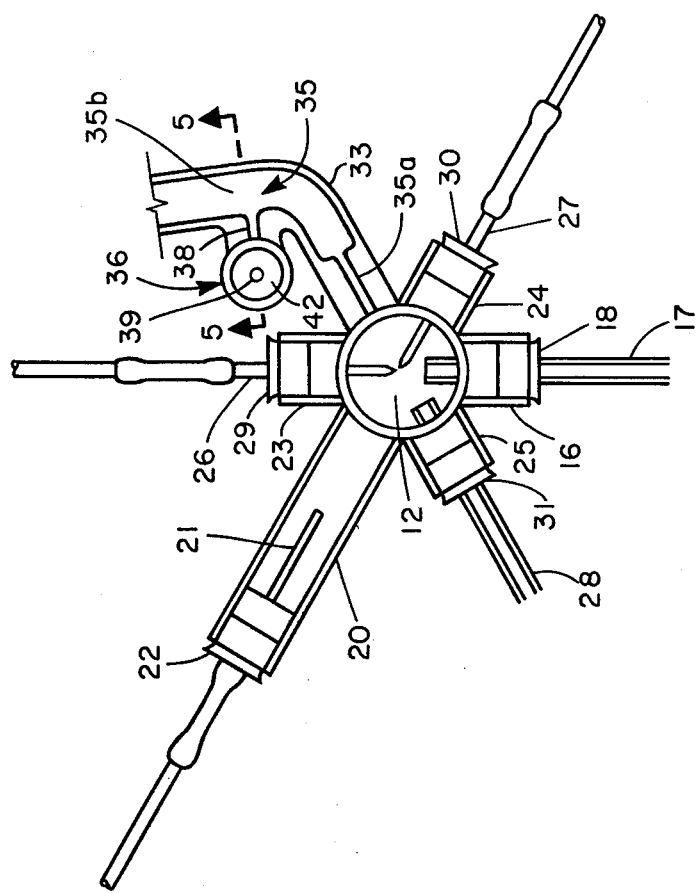
FIG. 4 is a partial top cross-sectional view as shown in FIG. 3 with electrodes and tubing added according to the present invention.
Figure 3:
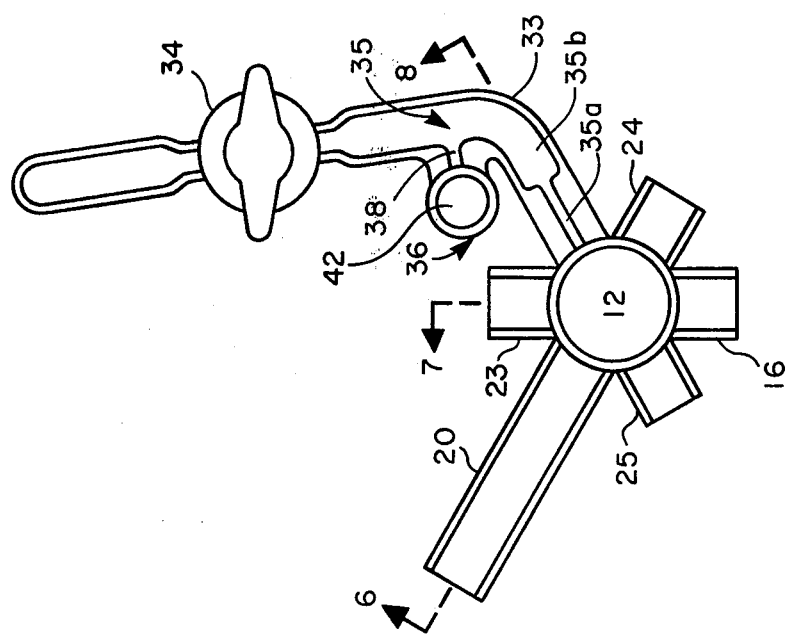
FIG. 3 is a top cross-sectional view taken along lines 3—3 of FIG. 2 including the drain tube of FIG. 1.
Figure 8:
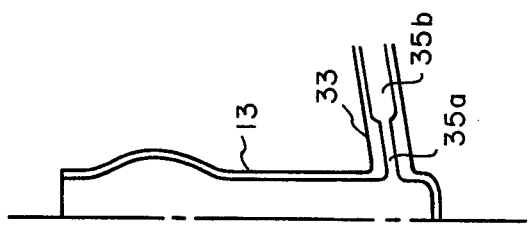
FIG. 8 is a cross-sectional view along a line 8 to the center axis in FIG. 3.
Figure 6:
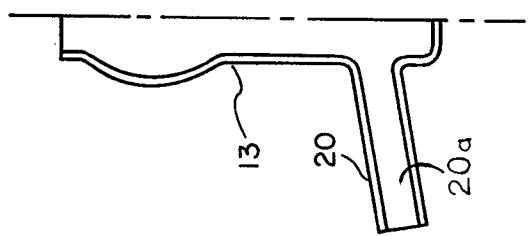
FIG. 6 is a cross-sectional view along line 6 to the center axis of the chamber in FIG. 3.

Not shown in FIGS. 1 and 2 but shown in FIGS. 3, 4 and 6, a side arm 20 is mounted on the lower portion of the vessel 13 to extend outward and downward to avoid capture of bubbles in the side arm 20a. As shown in FIG. 4, mounted into the end of the side arm 20 is an auxiliary first generating electrode 21 of a suitable metal. As mounted, the electrode 21 is in electrolytic communication through an open capillary, the passage 20a, with the contained electrolyte of the chamber 12. The auxiliary generating electrode 21 is removably mounted by means of septum 22 fitted into passage 20a. The septum 22 allows the replacement of the electrode 21 by withdrawing the electrode 21 through the septum 22 and inserting a new electrode in its place. Preferably, approximately 1.9 cm separates the end of the auxiliary generating electrode 21 and the chamber 12. The separation is to prevent rapid diffusion of the products generated at the electrode 21 into the contained electrolyte. The side arm 20 is filled with electrolyte to provide a liquid bridge which provides the electrolytic communication between the electrode 21 and the contained electrolyte of the chamber 12. The volume of electrolyte in the side arm 20 is not critical and is not considered part of the electrolyte contained by the chamber 12.

In FIGS. 1-4, additional inlet ports 23, 24 and 25 are provided through the cylindrical portion 13a of the vessel 13 for mounting a working generating electrode 26, a sensor electrode 27 and a tube 28 for adding electrolyte, respectively.

Figure 7:
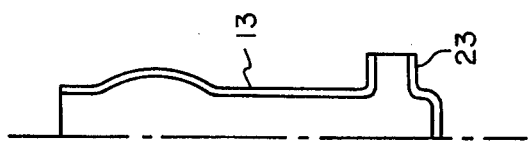
FIG. 7 is a cross-sectional view along a line 7 to the center axis in FIG. 3.

The working second generating electrode 26 is removably mounted through a septum 29 fitted in the inlet port 23 which is additionally shown in FIG. 7. The electrode 26 extends into the chamber 12 in the contained electrolyte and preferably, to the center of the chamber 12 and above the location at which the carrier fluid is introduced. The sensor electrode 27 is removably mounted through a septum 30 fitted in the inlet port 24. The sensor electrode 27 extends into the chamber 12 in the contained electrolyte and preferably, to the center of the chamber 12 and above both the location at which the carrier fluid is introduced and the working generating electrode 26. The level of the contained electrolyte can be at the level of the sensor electrode 27 or such that the sensor electrode 27 is in a froth of the electrolyte created by the stirring. Preferably, the level of the contained electrolyte is 2 to 3 mm above the sensor electrode 27. If the working generating electrode 26 is above the sensor electrode 27, the above statements as to the level of the contained electrolyte are true as to the working generating electrode 26 rather than to the sensor electrode 27.

Inlet port 25 and tube 28 are optional. Introduction of new electrolyte to chamber 12 during operation is optional but is preferred as it greatly lengthens the time the cell can be run without attention and for the present cell the introduction can be made without significantly affecting the titration time and sensitivity of the cell adversely. Electrolyte is evaporated during operation and without replenishment the level of electrolyte in the chamber 12 will fall until the exposure of an electrode or loss of a liquid bridge makes the cell inoperative. The tube 28 is replaceably mounted through a septum 31 mounted in inlet port 25. The tube 28 extends into the chamber 12 and electrolyte is introduced therethrough. For continuous flow of electrolyte, an outlet tube 46 is provided.

A drain tube 33, as shown in FIG. 1, 3, 4 and 8, is also mounted on the cylindrical portion 13a of the vessel 13 and extends outwardly and preferably upwardly. A stop cock 34 is provided in the drain tube 33. A passage 35 is provided in the drain tube 33 and extends through the length thereof and opens into the chamber 12 through a capillary without a fritted port or fiber wick. It should be observed that the passage 35 varies in cross-sectional area and has a relatively small diameter 35a where it enters the chamber 12 to slow diffusion of electrolyte and has a relatively large cross-sectional diameter at an intermediate portion 35b along the drain tube 33.

Figure 5:
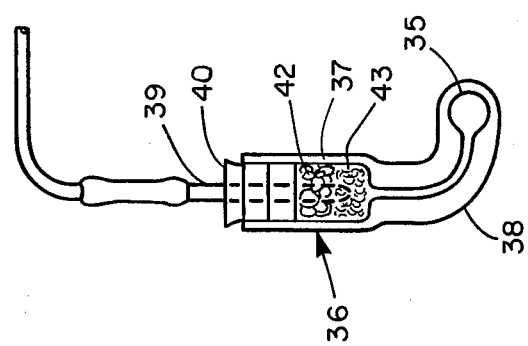
FIG. 5 is a cross-sectional view along lines 5—5 in FIG. 4.

A reference electrode assembly 36, as shown in FIG. 5, is connected to the drain tube 33. The reference electrode assembly includes a vertical arm 37 defining a compartment 42 and a vertically extending passage 38 which connects the compartment 42 to the enlarged portion 35b of the passage 35. The passages 38 and 35 form a liquid electrolyte bridge between the compartment 42 and the chamber 12. A reference electrode 39 is removably mounted to extend into the compartment 42 through a septum 40 fitted into the end of the compartment 42. As mounted, the reference electrode 39 is in electrolytic communication with the contained electrolyte in the chamber 12. Surrounding the tip of electrode 39 in compartment 42 is a suitable solution and below the solution is a permeable wall or plug 43 of glass wool to slow the diffusion of the solution. Preferably, the vertical arm 37 is further supported by an integral glass brace 41 which extends between the arm 37 and the vessel 13.

As an element of a means for maintaining a constant level of electrolyte, a further inlet port 45 is provided in the upper portion of the cylindrical portion 13a. The position of the inlet port 45 is not critical. The tube 46, mentioned before, is removably mounted through a septum 47 fitted in the inlet port 45. The tube 46 is extended into the chamber 12 so that its opening can be adjustably positioned at different levels in the chamber 12. The different levels result in different volumes of electrolyte being maintained in the chamber 12. The other end of the tube 46 is connected to a pump. The pump is operated in cooperation with a second pump connected to tube 28 through which electrolyte is introduced to the chamber 12 such that the amount of incoming electrolyte is not greater than the amount of electrolyte which can be withdrawn through tube 46. A typical introduction pumping rate is 0.1 ml/min. and withdrawal pumping rate is 0.1 ml/min. In continuous operation, the volume of electrolyte in the chamber 12 can be maintained at about six milliliters. If the volume is maintained at about three millimeters or as little as two milliliters or less, the titration time is shortened and the sensitivity increased. In applications in which the titration time is of little importance, the electrolyte volume can be maintained at volumes exceeding six milliliters. Suitable electronic circuitry for operating the aforedescribed electrolytic cell is set forth in U.S. Pat. 3,427,238 to Myers et al. and the teaching of that patent is incorporated herein by reference. It is noted that the Myers et al. cathode corresponds to the auxiliary generating electrode 21 herein and Myers et al. anode corresponds to the working generating electrode 26 herein. A description of the chemistry for a silver cell for chloride ion measurement can be found in U.S. Pat. No. 3,032,493 to Coulson and is hereby incorporated by reference.

A suitable tubing material for tubes 17, 28 and 46 in the cell is 1.6 mm OD Teflon tubing. A suitable septa material for the septum utilized is 6.4 mm OD silicone rubber backed with Teflon which has the Teflon contacting the electrolyte. The septa is punctured appropriately to accept the electrodes. The auxiliary generating electrode 21 is typically 0.5mm platinum wire while the other three electrodes are either all 0.5mm platinum (for sulfur analysis) or all 0.5mm fine silver rod (for chloride analysis). In previous cells, silver electrodes have been formed by coating silver on platinum. Such coating is unnecessary in the present invention. One of the advantages of the present cell is the ease with which it can be changed from one type of analysis to another by simply replacing the electrodes by withdrawing them from the septa.

Operation of the electrolytic cell is briefly described for a silver cell as follows. Let it be assumed that the vessel 13 has been filled with electrolyte through tube 28 or through the discharge port 14 to a suitable level as shown in FIGS. 1 and 2. Electrolyte is permitted to pass into side arm 20 by opening the stop cock 34. An original silver ion concentration is established and reflected in a potential between the sensor electrode 27 and the reference electrode 39 and measured by circuitry connected to the electrodes.

A carrier fluid containing the chloride to be titrated is then introduced to chamber 12 through tube 17. In the preferred case, the carrier fluid is an unreactive gas and serves as the primary means of stirring the contained electrolyte to ensure rapid and complete mixing of the chloride with the electrolyte.

As the sample enters the chamber 12 it goes into solution to produce a change measured by the circuitry in the electrical potential between the sensor electrode 27 and the reference electrode 39. This change in potential is caused by the precipitation, on a one to one basis, of silver ion by chloride ions. In brief, the apparatus circuitry in response to the change in potential causes a current to be applied across the auxiliary generating electrodes 21 and the working generating electrode 26 to generate new silver ions at the working generating electrode 26 as titrant to reestablish the original silver ion concentration and remove the change in potential. The current used is linear to the silver ion produced so the amount of chloride ion introduced is measured.

EXAMPLE I

Gas Chromatography

A cell according to the present invention was connected to circuitry as disclosed in the Myers patent for the purposes of titrating chlorinated hydrocarbons in a 70 cc/min. gas chromatographic helium effluent. The compounds eluded, for example, aldrin, lindane, were combusted at 800° C. in oxygen (100 cc/min) to produce combustion products, for example, $CO_2$, $H_2O$, $Cl_2$, and HCl. The combustion gases, the helium and remaining oxygen are introduced to the cell's carrier gas inlet tubing at the bottom of the cell. The electrolyte was 70% acetic acid in $H_2O$ and the reference solution was silver acetate. The electrolyte volume was initially 2ml. cell bias set at 260 millivolts amplifier gain set at 1000, and the recorder range set at 500 ohms. The chromatogram was displayed on a 1 milliwatt recorder with the result that differences of ± 0.2 nanograms of chloride in individual sample peaks were distinguishable above the background noise. Electrolyte maintenance was not utilized in these experiments, and due to electrolyte evaporation, the cell had to be manually replenished every two hours.

EXAMPLE II

Purgable Chloride Analysis

A cell as in Example 1, was connected to circuitry as disclosed in the Myers patent for the purpose of measuring the purgable organic halides in chlorinated drinking water. The compounds were continuously purged from a continuously pumped drinking water sample (approximately 5 ml/min.) run through a two stage sparge system (free $Cl_2$ was reduced to HCl so as not to interfere) with 50 cc/min of $O_2$ purge gas added per stage. The combined sparge flows were combusted at 800° C. with the addition of 100 cc/min additional dry $O_2$ flow. The combination products and remaining $O_2$ were introduced to the cell's carrier gas inlet tubing. The electrolyte volume was 6 ml of electrolyte (there is no compensation for electrolyte displaced by the electrodes or by the carrier gas), cell bias was set at 250 millivolts, the amplifier gain was set at 400, and the recorder range was set at 100 ohms. Continuous electrolyte maintenance (0.2 ml/min input) was utilized. The results were displayed on a 1 millivolt recorder such that a full scale reading represented 100 parts per billion. The sensitivity at low parts per billion input of chloride ion was ± 1 parts per billion. The analyzer was run continuously for two days unattended. In another run, the same cell ran without continuous electrolyte maintenance for about two hours without the necessity of electrolyte addition. The titration time with and without continuous electrolyte maintenance was approximately two minutes.

I claim:

1. An electrolytic cell for use in an electrolyte titration apparatus comprising:
    a. a vessel having a bottom and a sidewall defining a chamber for containing liquid electrolyte;
    b. means for introducing a carrier fluid containing a constituent to be titrated into contained electrolyte in said chamber;
    c. first and second generating electrodes mounted in electrolytic communication with the contained electrolyte in said chamber to generate titrant, said second generating electrode being mounted through said sidewall directly in said chamber to extend horizontally in the contained electrolyte;
    d. a sensor electrode mounted in said chamber to extend into the contained electrolyte;
    e. a reference electrode mounted in electrolytic communication with the contained electrolyte in said chamber; and
    f. means for introducing gas into said chamber for mixing, between horizontal stratas, the contained electrolyte therein without baffles.

2. An electrolytic cell according to claim 1 further including means for maintaining a constant level of contained electrolyte in said chamber.

3. A cell according to claim 2 further including means for mounting and removing said sensor electrode horizontally.

4. An electrolytic cell according to claim 1 wherein said sensor electrode is mounted above said second generating electrode and above the location at which the carrier fluid is introduced.

5. An electrolytic cell according to claim 4 wherein said second generating electrode is directly above the location at which the carrier fluid is introduced.

6. An electrolytic cell according to claim 1 wherein said sensor electrode and said second generating electrode are mounted to extend to the center of said chamber and the location at which the fluid containing the constituent to be titrated is introduced is near the center of said chamber.

7. An electrolytic cell according to claim 1 further including a compartment wherein said reference electrode is mounted, said compartment being in electrolytic communication with said chamber through an open capillary.

8. A cell according to claim 1 wherein said sensor electrode is rod-shaped.

9. A cell according to claim 1 wherein said second generating electrode is rod-shaped.

10. A cell according to claim 1 further including means for mounting and removing said second generating electrode horizontally.

11. An electrolytic cell for use in an electrolytic titration apparatus comprising:
   a. a vessel defining a chamber for containing liquid electrolyte;
   b. means for introducing a carrier fluid containing a constituent to be titrated into contained electrolyte in said chamber;
   c. first and second generating electrodes mounted in electrolytic communication with the contained electrolyte in said chamber to cause the generation of a titrant, said second generating electrode being mounted directly into said chamber to extend in the contained electrolyte;
   d. a sensor electrode mounted into said chamber in the contained electrolyte;
   e. a reference electrode mounted in electrolytic communication with the contained electrolyte in said chamber; and
   f. means for introducing and withdrawing electrolyte from said chamber to maintain a constant level of electrolyte in said chamber such that the electrolyte contained in said chamber is less than about three milliliters, said means including an inlet for introducing electrolyte to said chamber and an outlet for withdrawing electrolyte, said outlet being adjustably mounted in said chamber at the level to be maintained.

12. An electrolytic cell according to claim 10 further including a means to continuously withdraw electrolyte through said outlet and means to continuously introduce electrolyte through said inlet.

13. An electrolytic cell for use in an electrolytic titration apparatus comprising:
   a. a vessel having a bottom and a sidewall defining a chamber for containing liquid electrolyte;
   b. means for introducing a carrier fluid containing a constituent to be titrated into contained electrolyte in said chamber;
   c. means for removably mounting first and second generating electrodes in electrolytic communication with the contained electrolyte in said chamber to provide for the generation of a tritrant, and the second generating electrode being mounted through said sidewall directly into said chamber to extend horizontally in the contained electrolyte;
   d. means for removably mounting a sensor electrode horizontally into said chamber in the contained electrolyte;
   e. means for mounting a reference electrode in electrolytic communication with the contained electrolyte in said chamber; and
   f. means for introducing and withdrawing electrolyte from said chamber to maintain a constant level of electrolyte in said chamber such that the electrolyte contained in said chamber is less than about three milliliters.

14. An electrolytic cell for use in an electrolytic titration apparatus comprising:
   a. a vessel defining a chamber for containing liquid electrolyte;
   b. means for introducing a carrier fluid containing a constituent to be titrated into contained electrolyte in said chamber;
   c. first and second generating electrodes mounted in electrolytic communication with the contained electrolyte in said chamber to cause the generation of a titrant, said second generating electrode being mounted directly into said chamber to extend in the contained electrolyte;
   d. a sensor electrode mounted into said chamber in the contained electrolyte;
   e. a reference electrode mounted in electrolytic communication with the contained electrolyte in said chamber; and
   f. means for introducing and withdrawing electrolyte from said chamber to maintain a constant level of electrolyte in said chamber such that the quantity of electrolyte contained in said chamber and electrolyte providing the electrolytic communication with said first generating electrode and with the reference electrode is constant.

15. An electrolytic cell according to claim 14 wherein the means to maintain a constant level of contained electrolyte maintains a level such that the contained electrolyte in said chamber is less than about two milliliters.

16. An electrolytic cell according to claim 13 wherein said sensor electrode is mounted above said second generating electrode and above the location at which the carrier fluid is introduced.

17. An electrolytic cell according to claim 16 wherein said second generating electrode is directly above the location at which the fluid containing the constituent to be titrated is introduced.

18. An electrolytic cell according to claim 14 wherein said sensor electrode and said second generating electrode are mounted to extend to the center of said chamber and the location at which the carrier fluid is introduced is near the center of said chamber.

19. An electrolytic cell according to claim 14 further including a compartment wherein said reference electrode is mounted, said compartment being in electrolytic communication with said chamber through an open capillary.

* * * * *

UNITED STATES PATENT AND TRADEMARK OFFICE
CERTIFICATE OF CORRECTION

PATENT NO. : 4,133,733
DATED : January 9, 1979
INVENTOR(S) : Robert T. Moore

It is certified that error appears in the above-identified patent and that said Letters Patent are hereby corrected as shown below:

Column 6, line 26: Change "combination" to -- combustion --.

Column 6, line 37: Change "parts" to -- part --.

Column 8, line 4: Change "tritrant" to -- titrant --.

Signed and Sealed this

Twenty-seventh Day of November 1979

[SEAL]

Attest:

RUTH C. MASON
Attesting Officer

LUTRELLE F. PARKER
Acting Commissioner of Patents and Trademarks